US008834939B2

(12) United States Patent
Carty

(10) Patent No.: US 8,834,939 B2
(45) Date of Patent: Sep. 16, 2014

(54) AQUEOUS COMPOSITIONS OF COPPER SALTS AND HYDROGEN PEROXIDE

(75) Inventor: Peter Carty, Rowlands Gill (GB)

(73) Assignee: Probe Industries Limited, Tyne & Wear (GB)

( * ) Notice: Subject to any disclaimer, the term of this patent is extended or adjusted under 35 U.S.C. 154(b) by 0 days.

(21) Appl. No.: 13/201,136

(22) PCT Filed: Feb. 13, 2010

(86) PCT No.: PCT/EP2010/000905
§ 371 (c)(1),
(2), (4) Date: Sep. 21, 2011

(87) PCT Pub. No.: WO2010/091884
PCT Pub. Date: Aug. 19, 2010

(65) Prior Publication Data
US 2012/0014902 A1    Jan. 19, 2012

(30) Foreign Application Priority Data
Feb. 13, 2009  (GB) .................................. 0902429.0

(51) Int. Cl.
| | | |
|---|---|---|
| *A01N 59/20* | (2006.01) | |
| *A01N 39/00* | (2006.01) | |
| *A01N 59/02* | (2006.01) | |
| *A61K 33/04* | (2006.01) | |
| *A61L 9/00* | (2006.01) | |
| *A61L 11/00* | (2006.01) | |
| *A61L 9/01* | (2006.01) | |
| *A01N 25/00* | (2006.01) | |
| *A01N 25/24* | (2006.01) | |
| *A01N 59/00* | (2006.01) | |

(52) U.S. Cl.
CPC . *A61L 9/01* (2013.01); *A01N 59/00* (2013.01); *A01N 59/20* (2013.01)
USPC ........... 424/630; 424/616; 424/709; 424/713; 424/76.2; 424/76.5; 424/76.8; 424/405; 424/407

(58) Field of Classification Search
CPC ....... A01N 59/00; A01N 59/20; A01N 25/22; A01N 59/02; A01N 25/24; A01N 59/16; A61L 2/186; A61L 2/22
See application file for complete search history.

(56) References Cited

U.S. PATENT DOCUMENTS

| | | | |
|---|---|---|---|
| 3,793,294 A * | 2/1974 | Suling .............................. 526/91 |
| 4,586,982 A | 5/1986 | Poppel et al. | |
| 4,956,183 A | 9/1990 | Miki et al. | |
| 5,372,802 A | 12/1994 | Barrows et al. | |
| 5,525,123 A * | 6/1996 | Lorenz et al. ...................... 8/408 |
| 6,495,096 B1 | 12/2002 | Hamaguchi et al. | |
| 6,500,465 B1 | 12/2002 | Ronlan | |
| 7,012,053 B1 * | 3/2006 | Barnabas et al. ............. 510/287 |
| 2003/0151024 A1 | 8/2003 | Wegner | |
| 2006/0286051 A1 | 12/2006 | Tanaka et al. | |
| 2009/0074881 A1 | 3/2009 | Kielbania, Jr. | |

FOREIGN PATENT DOCUMENTS

| | | |
|---|---|---|
| DE | 10 2007 003693 A1 | 7/2008 |
| GB | 2345637 A | 7/2000 |
| JP | 10216697 A | 8/1998 |
| JP | 2009040760 A | 2/2009 |
| WO | 9304664 A1 | 3/1993 |
| WO | 2009032203 A1 | 3/2009 |

OTHER PUBLICATIONS

International Search Report for PCT/EP2010/000905, Completed by the European Patent Office on May 28, 2010, 3 Pages.

* cited by examiner

*Primary Examiner* — Brian-Yong Kwon
*Assistant Examiner* — Mark V Stevens
(74) *Attorney, Agent, or Firm* — Brooks Kushman P.C.

(57) ABSTRACT

Aqueous compositions, methods of manufacturing such aqueous compositions, and methods of removing reducing and/or suppressing malodors using such aqueous compositions are described. These compositions utilize a combination of hydrogen peroxide, a source of copper II, nonionic surfactant and alcohol to provide a highly effective and stable malodor removing, reducing and/or suppressing composition. The compositions are particularly useful as aerosol compositions for effective malodor removal, reduction and/or suppression in particular malodors from open sites such as landfill and in closed domestic environments such as the home. Also described is a stabilized hydrogen peroxide solution, which is stable on the addition of copper (II) salts.

15 Claims, No Drawings

AQUEOUS COMPOSITIONS OF COPPER SALTS AND HYDROGEN PEROXIDE

CROSS-REFERENCE TO RELATED APPLICATION

This application is the U.S. national phase of PCT Appln. No. PCT/EP2010/000905 filed Feb. 13, 2010 which claims priority to British application 0902429.0 filed Feb. 13, 2009, the disclosures of which are incorporated in their entirety by reference herein.

FIELD OF INVENTION

The present invention is concerned with aqueous compositions, methods of manufacturing such aqueous compositions and methods of removing and/or suppressing malodours using aqueous compositions.

BACKGROUND ART

Odours or malodours may be generated by many industrial processes and activities as well as occurring through other forms of human activity such as waste disposal into landfill as well as from natural sources.

A number of compositions, methods and processes have been developed in the art to deal with the problem of malodour generation. The source of the malodour is typically one or more of the following chemicals or class of chemicals; evil-smelling and toxic organic sulfur compounds, such as methylmercaptan, dimethyl sulfide and dimethyl disulphide, diallyl sulfide, ammonia, hydrogen sulfide, skatole (3-methyl indole) and the like. With these prior art solutions one strategy has been to treat and/or remove the chemical source of the malodour for example in a waste stream before release into the atmosphere. These strategies require the treatment of process waste streams, both liquid and gaseous before release into the atmosphere. Examples of such malodour control systems are: mist filtration, thermal oxidation/incineration, biofiltration, adsorption, wet scrubbing/absorption, chemical treatment and irradiation.

Despite the availability of various treatment strategies for industrial process waste streams malodour generation from such processes and their related waste continues to be a problem. In addition these solutions directed to industrial waste streams are not applicable to malodour control problems outside of the industrial plant in the open environment, where the malodour is from large area sources of varied and complex composition such as the malodours associated with landfill and other waste disposal sites. In addition these solutions directed to industrial waste streams are not applicable to malodour control problems associated in closed domestic environments where the sources of malodour can again be many and varied and in some instances difficult to determine.

With reference to the problem of malodours in the open environment, one solution is currently provided by Probe Industries and marketed under the trade name AiroNaut™. This solution utilizes spraying techniques where active compositions are deployed as ultra-fine droplets usually along the boundary lines of the area source to suppress malodours. The sprayer is a rotary atomizer, which uses centrifugal action to produce billions of droplets of aqueous composition in the form of a mist or fog.

With reference to the problem of malodours in the domestic environment there are many approaches to solving this problem. A wide variety of deodourizing compositions are known in the art, the most common of which contain perfumes to mask malodour. Odour masking is the intentional concealment of one odour by the addition of another. However preference to perfume is greatly varied and high levels are needed to ensure that the malodour is no longer noticeable. In addition masking does not actually remove the odourous compound or the source of the odour.

Odour modification, in which the odour is changed by, for example, chemical modification, has also been used. Current malodour modification methods known in the art are oxidative degradation, which uses oxidizing agents such as oxygen bleaches, chlorine, chlorinated materials such as sodium hypochlorite, chlorine dioxide and potassium permanganate to reduce malodour, and reductive degradation which uses reducing agents such as sodium bisulfite to reduce malodour.

Other methods of odour control utilize actives that are targeted to react with malodours having specific chemical functional groups. Examples of such actives are; biguanide polymers, which complex with organic compounds containing organically bound N and/or S atoms and fatty alcohol esters of methyl methacrylic acid which react with thiols, amines, and aldehydes. Such actives are limited in the scope of protection which they afford because they only react with limited types of malodour.

Other types of deodourizing compositions known in the art contain antibacterial and antifungal agents which regulate the malodour-producing microorganisms found on the surface to which the deodourizing composition is directed. Many skin deodourant products use this technology. These compositions are not effective on malodours that have already been produced and malodours that do not come from bacterial sources, such as tobacco, food odours or odours from open sources.

There is therefore a continuing need for alternative and/or more effective compositions and methods for open area source malodour control and for malodour control in the domestic environment.

DISCLOSURE OF THE INVENTION

The present invention relates to aqueous compositions that are suitable for removing, reducing and/or suppressing odours and malodours, to articles of manufacture comprising such compositions, methods of use of such compositions and methods of manufacture of such compositions including intermediate compositions for their manufacture. These compositions are based on the combination of copper (II) and hydrogen peroxide in relatively stable compositions. Under normal conditions of formulation the combination of soluble copper and hydrogen peroxide in an aqueous environment would be inherently unstable with the copper species catalyzing the decomposition of the hydrogen peroxide. The present invention through careful formulation and manufacturing procedures results in a relatively stable combination of soluble copper and hydrogen peroxide in a combined aqueous solution. In the compositions of the present invention the rate of decomposition, as evidenced by oxygen off gassing compared to a conventional mixture of these components is significantly reduced with compositions remaining active for long periods of time after formulation. The compositions are found to retain at least 75% of the active hydrogen peroxide component after one week of storage.

The odour-absorbing/suppressing compositions are designed to remove, reduce and/or suppress odours caused by a broad spectrum of organic odouriferous materials.

Thus in accordance with the present invention there is provided an aqueous composition comprising:
a) at least one source of copper,
b) hydrogen peroxide or a source of hydrogen peroxide, c) one or more alcohols, and
d) one or more surfactants.

This composition may be used as prepared in the form of a concentrate or it may be diluted with water prior to use. In one embodiment the composition is a malodour removing reducing or suppressing composition, preferably in the form of an aerosol.

The present invention further provides for a method for the manufacture of a composition concentrate according to the present invention, which method comprises:
a) preparing an aqueous solution comprising at least one alcohol, at least one surfactant and hydrogen peroxide, and
b) adding a source of copper (II) to the solution prepared in (a).

It has been found that the solution of step (a) is a particularly stable hydrogen peroxide solution. Thus the present invention further provides for a stabilized aqueous hydrogen peroxide solution comprising:
(i) hydrogen peroxide or a source of hydrogen peroxide,
(ii) one or more alcohols, and
(iii) one or more surfactants.

In a preferred method for the manufacture in step (a) the alcohol is added to the surfactant before addition of water with mixing. In a preferred embodiment the hydrogen peroxide is added to the alcohol/surfactant mixture before the addition of water with careful stirring. Water is preferably added to the mixture of alcohol, surfactant and hydrogen peroxide with mixing.

The source of copper is preferably copper (II), which may be added as a solid salt or other source of copper (II) to the mixture of step (a) in the method for the manufacture. The copper (II) source may be introduced and preferably is introduced as an aqueous copper (II) solution. The source of copper is typically a copper salt and preferably a copper (II) salt. Inorganic copper (II) salts suitable for use in the present invention include copper bromide, copper carbonate, copper nitrate, copper chloride and copper sulphate, with hydrated copper sulphate being the most preferred. Simple organic copper salts suitable for use in the present invention include, copper lactate, copper formate, copper oxalate, copper acetate, and copper citrate. The preferred soluble source of copper is one or more organic copper salts and most preferably is copper citrate. In some formulations a mixture of one or more inorganic and one or more organic copper (II) salts may be used; in this situation the preferred mixture is a copper sulphate/copper citrate mixture.

When used the aqueous copper (II) solution is added to the solution prepared under step (a) of the method with stirring. The preparation of all solutions is preferably undertaken under ambient conditions of temperature and pressure with no requirement for temperature control. An ideal mixing unit comprises an SS propeller/stirrer powered by an electric motor in covered stainless steel tanks. When a solid source of copper (II) is used i.e. a salt then this may be added in a number of approximately equal proportions with stirring. It has been found that in some instances that organic copper (II) compounds such as copper citrate for example are difficult to dissolve in the mixture of step (a) or aqueous media prepared before addition to the mixture of step (a). In these situations it has been found that dissolution and formation of the active component on addition of the copper (II) source to the mixture of step (a) is greatly improved if an approximately equimolar amount of the sodium or potassium salt of the acid is added in addition to the copper salt. As an example when copper citrate is used an equimolar amount of sodium citrate addition aids dissolution and formation of the active composition. It is preferred that when the copper source is such an organic acid salt that this is used in combination with a comparable or compatible sodium or potassium salt of the organic acid. It is envisaged that the sodium salt may not be of the same organic acid.

When the aqueous copper solution is mixed with the solution prepared under step (a) at temperatures in excess of 5° C., a brown precipitate may be formed. It is believed that this is a precipitate of a copper (II) peroxy complex. This precipitate may often be observed when copper sulphate is used as the copper source. In a preferred embodiment when such a precipitate is formed a suitable buffering organic acid may be added to the mixture. A preferred organic acid is citric acid, which may be added to the mixture to aid dissolution of the precipitate and formation of the active composition. The suitable buffering organic acid may be added to the mixture within the range 0.05 to 1 wt %, preferably 0.1 to 0.75 wt %, more preferably 0.1 to 0.5 wt % and most preferably 0.15 to 0.35 wt % of the composition.

On completion of the method for the manufacture the resulting blue solution is a concentrated solution containing at least 1% by weight of hydrogen peroxide. The concentrated solution is stable with little or no change in colour even after several months of storage. This concentrate may now be used to manufacture malodour removing or suppressing compositions according to the present invention by simple dilution with water to the required concentration of copper and/or hydrogen peroxide. For some applications the composition may be used neat without dilution, especially with difficult to treat odorous situations.

Suitable surfactants are nonionic surfactants, anionic surfactants, cationic surfactants, amphoteric surfactants, zwitterionic surfactants, and mixtures thereof. However, it is most preferred that the surfactant comprises one or more nonionic surfactants. When a surfactant containing one, or more, aliphatic alkyl group is used, it is preferred that it contain relatively short alkyl chains of from about 5 to about 22 carbon atoms. When used preferred anionic surfactants are dialkyl sulfosuccinate, alkylarylsulfonate, fatty alcohol sulfate, paraffin sulfonate, alkyl sarcosinate, alkyl isethionate salts having suitable cations, e.g., sodium, potassium, alkanol ammonium, etc., and mixtures thereof. Preferred amphoteric surfactants are the betaines. It is preferred that the surfactant have good wetting properties. Also preferred are surfactants that have the hydrophilic groups situated between hydrophobic chains, such as Pluronic RX surfactants, Surfynol surfactants, polyethylene glycol diesters of fatty acids, fatty acid esters of ethoxylated sorbitans. dialkvl sulfosuccinate, di(C8-C12 alkyl)di(C1-C2 alkyl)ammonium halides. and mixtures thereof; or surfactants that have the hydrophobic chains situated between hydrophilic groups, such as Pluronic surfactants; and mixtures thereof. Mixtures of these surfactants and other types of surfactants are also preferred to form no-foaming or low-foaming solubilizing agents.

It is preferred that the surfactant is a non-ionic surfactant. Examples of suitable non-ionic surfactants include those based on: alkyl poly(ethylene oxide); alkylphenol poly(ethylene oxide); copolymers of poly(ethylene oxide) and poly(propylene oxide) (commercially called Poloxamers or Poloxamines); alkyl polyglucosides, including for example octyl glucoside, decyl maltoside; fatty alcohols such as for example cetyl alcohol and oleyl alcohol, cocamide MEA, cocamide DEA; polysorbates such as Tween 20 and Tween 80; dodecyl dimethylamine oxides and alcohol ethoxylates. The preferred non-ionic surfactants are alcohol ethoxylates of the following general structure (I):

$$R-(OCH_2CH_2)_n-OH \qquad (I)$$

Wherein R is an alkyl group of the parent alcohol and n=number of molecules of ethylene oxide present. Preferably R is a hydrocarbon group having from 5 to 22 carbon atoms ($C_8$ to $C_{22}$ alkyl group) and may be a branched or linear alkyl group. The surfactant may comprise a mixture of compounds of general structure (I) having one or more different hydrocarbon groups. Preferably the surfactant has a hydrocarbon group R having from 8 to 22 carbon atoms, more preferably having from 8 to 15 carbon atoms and more preferably 9 to 11 carbon atoms. Preferably n is from 3 to 40, more preferably from 3 to 30, more preferably from 3 to 20, more preferably from 5 to 10 and most preferably from 5 to 9. One preferred surfactant has an n value of 6.5. Preferred nonionic surfactants are polyethylene glycol-polypropylene glycol block copolymers, such as PluronicX and Pluronic RX surfactants from BASF; TetronicX and Tetronic RX surfactants from BASF, ethoxylated branched aliphatic diols such as SurfynolX surfactants from Air Products; ethoxylated alkyl phenols, such as IgepalX surfactants from Rhone-Poulenc; ethoxylated aliphatic alcohols and carboxylic acids; polyethylene glycol diesters of fatty acids; fatty acid esters of ethoxylated sorbitans; and mixtures thereof. The most preferred surfactants are nonionic ethoxylated 8 to 15 carbon atom aliphatic alcohols with from 5 to 10 ethoxyl units.

The alcohol may be a simple aliphatic alcohol, diol or polyol. The most preferred alcohols are diols. The preferred diols are low molecular weight diols having from 3 to 10 carbon atoms in the alkyl moiety. The most preferred diols are vicinal diols such as for example propane-1,2-diol (monopropylene glycol), which is the most preferred diol.

The hydrogen peroxide preferably used as an aqueous composition having from 10 to 50% by weight of hydrogen peroxide in water. The hydrogen peroxide composition is preferably from 20 to 40% by weight hydrogen peroxide, more preferably from 25 to 40% and most preferably from 30 to 40% by weight hydrogen peroxide. A suitable composition is approximately 35% by weight hydrogen peroxide.

The composition concentrate according to the present invention may comprise from 1 to 20%, more preferably 1 to 10%, more preferably 2 to 10% and most preferably 3 to 6% by weight of hydrogen peroxide present as a complex with copper (II). In some applications the undiluted concentrate may be used for malodour suppression. However, it is preferred that the concentrate is diluted and that the concentration of hydrogen peroxide in the final composition is 5% or less by weight. Thus the concentrate may be diluted to provide a malodour removing or suppressing composition according to the present invention. Typically compositions with up to 3% by weight hydrogen peroxide, more preferably up to 2% by weight of hydrogen peroxide and most preferably up to 1.75% by weight hydrogen peroxide may be used for the suppression and/or removal, reduction of strong malodour from compost leachates, land-fill sites, lagoon treatment, sewage storage tanks etc and at this concentration the composition is typically not deployed in the form of an aerosol but is deployed by liquid injection, drip feed or liquid spraying techniques. In a preferred embodiment the composition is at a dilution providing 1% or less by weight of hydrogen peroxide, preferably 0.5% or less by weight of hydrogen peroxide, more preferably 0.1% or less by weight and most preferably 0.055% by weight or less of hydrogen peroxide. At these low levels of hydrogen peroxide the composition is ideally suited for application as an aerosol through a rotary atomizer systems similar to that used for the deployment of AiroNaut™ compositions, although stronger solutions may be used. These solutions may also be dispensed through a propellant driven aerosol or mechanical aerosol container suitable for domestic use. At a concentration of 0.15% the aerosol contains 1500 ppm of hydrogen peroxide. At a concentration of 0.0525% by weight hydrogen peroxide the aerosol contains 525 ppm of hydrogen peroxide. It is preferred that the aerosol compositions of the present invention have 2000 ppm or less of hydrogen peroxide, preferably 1500 ppm or less of hydrogen peroxide, more preferably 550 ppm or less of hydrogen peroxide, more preferably 200 ppm or less and most preferably 150 ppm or less of hydrogen peroxide.

In the compositions of the present invention it is preferred that the alcohol is present at a concentration of 20% or less by weight based on the total weight of the composition, preferably 15% or less by weight, more preferably 12% or less by weight and most preferably 10% or less by weight.

In the compositions of the present invention it is preferred that the surfactant is present at a concentration from 1 to 55% by weight based on the total weight of the composition. Preferably, it is present at a concentration from 2 to 45% by weight, more preferably 2 to 30% by weight, more preferably 2 to 20% by weight, more preferably 2 to 15% by weight and most preferably 2 to 12% by weight. One preferred composition comprises 3 to 12% by weight of surfactant.

In the compositions of the present invention the amount of copper (II) present is dependant on the level of hydrogen peroxide in the composition. Preferably the amount of copper (II) present in the composition is selected to provide a mole ratio of copper (II) to hydrogen peroxide within the range of 1:50 to 1:200 and more preferably within the range of 1:75 to 1:150. One preferred composition comprises a mole ratio of copper (II) to hydrogen peroxide of 1:100. In the compositions of the present invention the balance of the composition in order to achieve a 100% by weight composition is water.

In a further aspect the composition may further comprise one or more cyclodextrins. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structures with hollow interiors of specific volumes. The "lining" of each internal cavity is formed by hydrogen atoms and glycosidic bridging oxygen atoms; therefore, this surface is fairly hydrophobic.

The cavities within the cyclodextrin in the solution of the present invention should remain essentially unfilled (the cyclodextrin remains uncomplexed) while in solution, in order to allow the cyclodextrin to absorb various odour molecules when the solution is applied to a surface.

Preferably, the cyclodextrins used in the present invention are highly water-soluble such as, alpha-cyclodextrin and/or derivatives thereof, gamma-cyclodextrin and/or derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a —CH2-CH(OH)—CH3 or a —CH2CH2-OH group; branched cyclodextrins such as maltose-bonded cyclodextrins; cationic cyclodextrins such as those containing 2-hydroxy-3-(dimethylamino)propyl ether, wherein R is CH2-CH(OH)—CH2-N(CH3)2 which is cationic at low pH; quaternary ammonium, e.g., 2-hydroxy-3-(trimethylammonio)propyl ether chloride groups, wherein R is CH2-CH(OH)—CH2-N(CH3)3C; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. The availability of solubilized, uncomplexed cyclodextrins is beneficial for effective and efficient odour control performance when used in combination with copper (II) and hydrogen peroxide in the composition of the present invention. Solubilized, water-soluble cyclodextrin can exhibit more efficient odour control performance than non-water-soluble cyclodextrin when deposited onto surfaces.

Examples of preferred water-soluble cyclodextrin derivatives suitable for use herein are hydroxypropyl alpha-cyclodextrin, methylated alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-[beta]-cyclodextrin, commonly known as DIMEB, in which each glucose unit has about 2 methyl groups with a degree of substitution of about 14. A preferred, more commercially available, methylated beta-cyclodextrin is a randomly methylated beta-cyclodextrin, commonly known as RAMEB, having different degrees of substitution, normally of about 12.6.

It is also preferable to use a mixture of cyclodextrins. Such mixtures absorb odours more broadly by complexing with a wider range of odouriferous molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, more preferably a mixture of alpha-cyclodextrin, or an alpha-cyclodextrin derivative, and derivatised beta-cyclodextrin, even more preferably a mixture of derivatised alpha-cyclodextrin and derivatised beta-cyclodextrin, most preferably a mixture of hydroxypropyl alpha-cyclodextrin and hydroxypropyl beta-cyclodextrin, and/or a mixture of methylated alpha-cyclodextrin and methylated beta-cyclodextrin.

The composition of the present invention can also be used in an article of manufacture comprising said composition plus a spray dispenser. When the commercial embodiment of the article of manufacture is used, it is optional, but preferable, to include the preservative. Therefore, the most basic article of manufacture comprises a composition according to the present invention and a dispenser, which may be a liquid dispenser, a spray dispenser or a foam dispenser. The article of manufacture herein may comprise any suitable liquid, spray or foam dispenser. More preferably, the spray dispenser is a non-aerosol, manually activated or mechanically pumped, pump-spray dispenser. Said pump-spray dispenser my comprise a container and a pump mechanism which securely screws or snaps onto the container. The container comprises a vessel for containing the composition to be dispensed.

In a further embodiment the present invention provides a method of malodour control, which method comprises deploying a malodour removing reducing or suppressing composition according to the present invention to a source of malodour in the form of a liquid, a foam or an aerosol. Preferably the composition is deployed as an aerosol. Thus the composition of the present invention may be used by distributing, e.g., by placing the aqueous solution into a dispensing means, preferably a spray dispenser and spraying an effective amount onto the desired surface or article. An effective amount as defined herein means an amount sufficient to remove, reduce or suppress odour to the point that it is not discernible by the human sense of smell. In a preferred embodiment the composition is delivered to the malodourous atmosphere as an aerosol through a rotary atomizer system.

Thus the present invention relates to the method of spraying a mist or aerosol of an effective amount of composition into the air to remove, reduce or suppress malodour. application as an aerosol through a rotary atomizer systems The present invention also provides a odour malodour removing reducing or suppressing kit comprising a stabilized hydrogen peroxide composition as described herein and a separate copper (II) solution. In this form the kit may be supplied to end users and the two compositions may be mixed in appropriate proportions just prior to utilization for the removing reducing or suppressing of malodour. The kit will have a longer shelf life than the combined solutions and in kit form there is more flexibility for the end user to alter the proportions of copper to hydrogen peroxide in the final composition for any given malodour removing reducing or suppressing scenario. Formulation flexibility is further achieved by dilution of both or either of the kit parts with water before use.

The invention is further illustrated and will be further understood with reference to the following examples.

EXAMPLE 1

A copper containing composition was prepared as follows: 20 L of monopropylene glycol was added to a first container equipped with a mixer containing 24 L of non-ionic surfactant (SURFAC UN65/95, which is a C9-11 alcohol with 6.5 moles ethylene oxide, 95% active in 5% water, as supplied by Surfachem Group Ltd, 100 Wellington Street, Leeds, West Yorkshire, LS1 4LT, United Kingdom), with stirring. 30 L of hydrogen peroxide (35% in water) was added to the container with mixing for 20 minutes. This mixture is a stabilized hydrogen peroxide solution. A second container was charged with 300 L of water and the contents of the first container were pumped into the second container. 0.763 Kg of hydrated copper sulphate ($CuSO_4.5H_20$) was added to the first container and dissolved in 50 L of water, with stirring for 10 mins after which the copper sulphate solution was pumped from the first container to the second container with stirring. The volume of the composition in the second tank was adjusted to 700 L with water.

As transfer of the copper sulphate solution was near completion a brown colour developed within the composition in the second container and this persisted for at least 10 hours. The composition in the second container also gave off a gas (oxygen) and the brown colour began to fade after about 4 hours. The solution was allowed to stand for over 48 hours and the remaining brown solution was stable indefinitely. The pH of the final composition was 4.5. Although this composition was relatively unstable the composition as produced and diluted was effective in removing and/or suppressing malodours.

EXAMPLE 2

A copper containing composition was prepared as follows: 20 L of monopropylene glycol was added to a first container equipped with a mixer containing 24 L of nonionic surfactant (SURFAC UN65/95, which is a C9-11 alcohol with 6.5 moles ethylene oxide, 95% active in 5% water, as supplied by Surfachem Group Ltd, 100 Wellington Street, Leeds, West Yorkshire, LS1 4LT, United Kingdom), with stirring. 30 L of hydrogen peroxide (35% in water) was added to the container with mixing for 20 minutes. A second container was charged with 300 L of water and the contents of the first container were pumped into the second container. 0.763 Kg of hydrated copper sulphate ($CuSO_4.5H_2O$) was added to the first container and dissolved in 50 L of water, with stirring for 10 mins after which the copper sulphate solution was pumped from the first container to the second container with stirring. The volume of the composition in the second tank was adjusted to 700 L with water. As transfer of the copper sulphate solution was near completion a brown colour developed within the composition in the second container.

After addition of the copper sulphate solution was completed 2.002 Kg of citric acid was added to the second container composition in 250 g portions with stirring. On completion of the addition of citric acid the brown colour disappeared and the final composition was a blue colour typical of copper (II) solutions. The pH of the final composition was measured at 2.5. The final composition was stable and did not produce off gases. Although not wishing to be bound by theory it is believed that the citric acid buffered the composition and stabilized the copper peroxide complex formed during manufacture of the composition. The composition was found to be particularly active in removing malodours.

EXAMPLE 3

100 ml aliquots of the brown suspension/solution as prepared according to Example 1 were treated with appropriate amounts of solid citric acid and the time taken for the brown discolouration to disappear and for the composition to turn pure blue was determined and recorded.
1. 100 ml brown solution=1 g of citric acid crystals took 10 minutes
2. 100 ml brown solution=2 g of citric acid crystals took 7 minutes
3. 100 ml brown solution=8 g of citric acid crystals took 5 minutes.

For the large scale preparation of the composition citric acid should be used to lower the pH and to speed up the rate of reaction converting brown copper peroxide to a pure blue solution. The pure blue solution is more stable and superior for odour control than the brown suspension/solution.

EXAMPLE 4

A copper free composition was prepared as follows: 0.6 L of non-ionic surfactant (Surfac UN65/95) and 0.5 L of monoproplyeneglycol were mixed together in a large beaker. To this mixtures was added 0.75 L of hydrogen peroxide (35% hydrogen peroxide) with stirring, which resulted in a temperature rise of about 10° C. To this mixtures was added 3.150 L of distilled water with make up to a final composition volume of ~5 L.

EXAMPLE 5

Sample of liquid/solid waste from an abattoir was available and was used as a control; 4 ml of the sample of foul smelling suspension was placed on clean paper towels. The compositions of Example 2 and Example 4 were introduced to a spraying apparatus and one spray of each composition was applied to the foul smelling samples on the paper towels. Six individuals were then asked to assess the residual odour. All six individuals (3 female and 3 male) selected the copper-containing formulation as giving the least residual odour. This indicates that the composition containing copper is much better at controlling odour than the copper-free composition.

EXAMPLE 6

Six solutions were prepared using fixed weights of copper (II) sulphate with variable weights (concentrations) of hydrogen peroxide solution. The fixed weight of copper sulphate was 2.5 g dissolved in 25 ml distilled water and the varying hydrogen peroxide concentrations were prepared as follows:—

| Sample No | $Cu:H_2O_2$ (molar ratios) | Vol 35% $H_2O_2$ + Vol $H_2O$ | Vol % $H_2O_2$ |
|---|---|---|---|
| 1 | 1:100 | 90 ml + 10 ml | 25.2 |
| 2 | 1:50 | 44 ml + 56 ml | 12.32 |
| 3 | 1:25 | 22 ml + 78 ml | 6.16 |
| 4 | 1:20 | 18 ml + 82 ml | 5.04 |
| 5 | 1:10 | 9 ml + 91 ml | 2.52 |
| 6 | 1:5 | 4.5 ml + 95.5 ml | 1.26 |

These hydrogen peroxide solutions were all made up to 100 ml and the total volume of copper solution plus peroxide solution was 125 ml. The copper sulphate solutions were added to the appropriate peroxide solutions with stirring.

During preparation and mixing none of these six solutions produced a brown colour; the only colour was that of the copper sulphate. This confirms that the brown discoloration was not produced as a result of the combination of these components.

To each solution was added 5 ml of monopropylene glycol and no colour change was observed. To each solution was added 5 ml of nonionic surfactant (Surfac 65/95) and there was an immediate generation of a brown/green colour. Solutions 1-4 gave the most intense colour and 5 and 6 the least colour. These colour persisted for at least 4 hours at room temperature.

Although the mechanism is not understood it is clear that at the prevailing pH of these compositions the surfactant has a role in the generation of the brown colour formation with copper and hydrogen peroxide. The reasons for this are unclear at present. The brown colour decreased with decreasing hydrogen peroxide concentration indicating that the formation of this brown/green colour is also related to the relevant surfactant and hydrogen peroxide concentrations.

EXAMPLE 7

Separate solutions were prepared of surfactant and hydrogen peroxide.

Surfactant solution: 4.5 ml Surfac+45.5 ml water=50 ml pH=5
Hydrogen peroxide Solution: 1.94 ml (35%) peroxide+48 ml water=50 ml pH=5
These solutions were mixed together to give 100 ml of solution with an approximate molar ratio of 1 Surfac:2 peroxide.
0.86 g of copper sulphate pentahydrate was added to the combined solution. The solution became green and pH dropped to 4.
This experiment was repeated with a 20 fold increase in the amount of hydrogen peroxide used.
4.5 ml Surfac+45.5 ml water=50 ml
20 ml peroxide+30 ml water=50 ml pH=3
The same mass of copper sulphate was added and this time there was no change in colour and the solution remained pure blue. Thus there was no colour change and no formation of other copper compounds with this excess amount of peroxide.

EXAMPLE 8

0.4 L of nonionic surfactant (SURFAC 65/95) was mixed with 1.2 Lo water in a 5 L plastic container and no excess foaming was observed at this stage. To this mixture was added 0.2 L of 35% hydrogen peroxide with careful mixing and a little more foaming occurred at this stage. To this mixture was added 0.04 L of monopropylene glycol with mixing. There was some foaming and what appeared to be a cloudiness appeared on the surface of the formulation. After ~⅔ hours the surface cloudiness was much less and the quantity of foaming had reduced.

This copper free composition was compared against a commercial odour suppressing product called Tego Sorb® (Evonik Industries). The comparison indicated that there was little difference between the two in terms of odour suppression.

A further experiment using copper sulphate mixed into the composition in a slightly diluted formula, still had poor odour-reducing properties. This result indicated that the order of addition of the components in the manufacture of the composition of the present invention is critical to achieve an active composition. In this example the hydrogen peroxide was added to an aqueous mixture of surfactant followed by the monopropylene glycol. Foaming was observed and cloudiness suggesting decomposition of the hydrogen peroxide addition of the copper sulphate to this composition did not result in the formation of the active copper hydrogen peroxide component observed in Example 1 or 2.

EXAMPLE 9

The following composition was prepared.

|  | ml | vol % |
| --- | --- | --- |
| SURFAC | 600 | 12 |
| MPG | 500 | 10 |
| H$_2$O$_2$(35%) | 143 | 10 |
| H$_2$O | 3687 | ~49 |
|  | 4930 |  |
| CuSO$_4$5H$_2$O 4 g in 70 ml |  |  |

The monopropylene glycol (MPG) was added to the nonionic surfactant (SURFAC) with stirring and easily mixed and dissolved. Then the hydrogen peroxide was carefully added to this mixture and again easily mixed into the solution. At this stage the pH was pH=5. To this mixtures was added the distilled water and finally the copper sulphate as solution dissolved in 70 ml of water was added. No precipitate or discolouration was apparent and a pale blue solution formed with no gassing. This experiment was repeated but this time with the addition of 19 g of hydrated copper sulphate in solution in 70 ml water. Immediate brown precipitate was formed which dissolved and the solution went pure blue after the addition of 20 g of citric acid. pH at the end of the experiment was 2-3.

The high level of copper compared to hydrogen peroxide is believed to have resulted in the formation of the undesirable brown precipitate, which is then taken onto solution in this copper sulphate system by addition of citric acid.

EXAMPLE 10

A composition as indicated below was prepared in order to provide nonionic surfactant:monopropylene glycol:hydrogen peroxide in the mole ratios of 2:6:6, which for a 2% hydrogen peroxide solution reduces to the following percentage composition excluding copper sulphate and citric acid:—

|  | % | ml |
| --- | --- | --- |
| Surfac | 8 | 80 |
| MPG | 4.6 | 46 |
| H$_2$O$_2$ | 2 | 57(35%) |
| Water | 85.4 | 817 |
|  | 100 | 1000 |

The composition was prepared as follows: A premixed of Surfac (160 ml), MPG (92 ml), hydrogen peroxide (114 ml of 35% solution) and water (1634 ml) was prepared as in Example 9. To this premix was then added citric acid solution (5.7 g in ~20 ml water) and finally pure copper sulphate (2 g in ~50 ml). During mixing there were no problems with excessive foaming or precipitation of brown copper peroxide.

EXAMPLE 11

To 400 ml of Surfac was added 230 ml of MPG. Hydrogen peroxide (35%) 285 ml was added and ~3 liters of water added. 25 g of citric acid in 75 ml of water and 12.5 g of copper sulphate hydrate dissolved in 100 ml water were added. The rest of the water (up to 5 liters) was added. The pure blue solution was stable and did not produce oxygen on standing.

EXAMPLE 12

Surfac (50 ml) plus MPG (29 ml) plus 35% hydrogen peroxide (57 ml). All mixed together as per usual. Weighed out 3.4 g copper citrate and tried to dissolve it in citric acid solution but would not dissolve. Added 10 g of sodium citrate in 50 ml water and added to the bulk formulation and the pale green/blue solution formed with pH=6.

Tested using stink bomb as a source of H$_2$S and ammonia. Broke stink bomb in enclosed room of approximately 15 m3. Left for one minute. Sprayed solution into headspace and closed the door. Left for one minute to act. Opened door and level of odour was detected subjectively. The solution appeared to have significantly reduced the level of odour, especially the ammonia.

EXAMPLE 13

A similar composition to previous examples was prepared using a replacement surfactant. The surfactant used was Imbentin-AGS/55, a low odour non-ionic surfactant (a liquid $C_{11}$-$C_{15}$ alcohol with 9 EO's) as supplied by Kolb-Switzerland. The formulation for the premix was as follows:—

|  | vol % | ml |
|---|---|---|
| Imbentin | 5 | 50 |
| MPG | 3 | 30 |
| $H_2O_2$(35%) | 1.5 | 43 |
| Water | 89 | 862 |
| Copper solution | 1.5 | 15 |
|  |  | 1000 |

For a concentration of 350 ppm copper ion from copper citrate, 1.05 g of pure copper citrate was helped to dissolve using sodium citrate in approx 15 ml water to give a pure blue aqua/water colour.

The mixing was OK with virtually no degassing and no separation into layers. The formulation was tested neat and at a 5:1 dilution with hydrogen sulphide and ammonia from "stink bombs". The test was carried out in a confined space (small room) and both the neat and 50% diluted compositions were effective against hydrogen sulphide and ammonia when the container and surrounding air were sprayed with the composition. The test was repeated with the leachate and again both products were effective, the neat formulation being a little better than the 5:1 dilution.

EXAMPLE 14

A similar composition to previous examples was prepared using a replacement surfactant. This surfactant Surfac 90/90 was supplied by Surfachem Group Ltd, 100 Wellington Street, Leeds, West Yorkshire, LS1 4LT, United Kingdom and was a $C_9$-$C_{11}$ alcohol ethoxylate with 9 ethylene oxide groups. This surfactant was used along to make one formulation having 500 ppm $Cu^{2+}$ from copper sulphate and a further formulation having 500 ppm $Cu^{2+}$ from copper citrate. Testing with foul smelling abattoir liquid on for most of a day showed that the citrate derived formulation was superior to the sulphate derived formulation.

EXAMPLE 15

Various formulations were prepared incorporating beta-cyclodextrin.
Stabilized Hydrogen Peroxide Composition

|  | vol % | ml |
|---|---|---|
| Surfactant | 5 | 50 |
| MPG | 3 | 30 |
| $H_2O_2$(35%) | 1.5 | 43 |
| Water | 90.5 | 877 |
|  | 100 | 1000 |

The cyclodextrin used was CAVASOL® W7 HP as supplied by Wacker Chemie AG, Burghausen, Germany. This product is a hydroxypropyl beta-cyclodextrin. To achieve a cyclodextrin concentration of 0.09 wt %, 0.9 g (900 ppm) per L of CAVASOL was added to stabilized hydrogen peroxide composition. To achieve a soluble copper level of 350 ppm $Cu^{2+}$ 1.05 g per L of copper citrate was added to the stabilized hydrogen peroxide composition. To aid dissolution of the copper citrate an additional equivalent amount of sodium citrate was used, the solution being made up in 20 ml of hot water with constant stirring.

For testing purposes the following compositions at a volume of 1 L were prepared:
1. Stabilized hydrogen peroxide composition with copper and cyclodextrin.
2. Stabilized hydrogen peroxide composition with copper but without cyclodextrin
3. Stabilized hydrogen peroxide composition without copper but with cyclodextrin The solutions were stable after cyclodextrin addition. Two types of odour tests were carried out using commercial 'stink bombs' in a confined space and foul-smelling abattoir liquor on paper towels.

These tests established qualitatively that the combination of copper ion/hydrogen peroxide with cyclodextrin when used in the neat undiluted form outperformed 50/50 diluted formulations in both experiments. Indeed in the foul-liquor tests the copper/hydrogen peroxide cyclodextrin system immediately eliminated all foul odours coming from the liquor-soaked paper towel. This shows that the combination of copper/hydrogen peroxide with cyclodextrin is particularly beneficial for the reduction of odour from very severe odour sources.

EXAMPLE 17

Experiments with Draeger® Tubes for Hydrogen Sulphide and Ammonia

Using commercial 'stink bombs' as a source of hydrogen sulhpide and ammonia experiments were carried out to determine reductions in levels of these two gases using the composition of the present invention as typically prepared according to Example 15 without the addition of cyclodextrin.

Apparatus

Clean 25 L plastic drums were used as the 'container' for the experiments. These were adapted to enable the headspace properties within the containers to be measured using Draeger® Tubes. A thin polythene film used as a closure to the container to contain the gases during the tests. Stink bombs were broken into the plastic drum, which was immediately sealed and 90 seconds was allowed for the odour to develop. The levels of gasses were measured with the Draeger® Tubes and after introduction by spraying of the composition of the present invention neat, at 50% dilution and 25% dilution.

Results (all Readings in ppm)

| Composition |  | $NH_3$ (ppm) | $H_2S$ (ppm) |
|---|---|---|---|
| Neat | CONTROL | >100 | 220 |
|  | With Composition | 23 | 5 |
|  | Reduction (%) | >77 | 98 |
| 50% dilution | CONTROL | >100 | 250 |
|  | With Composition | 30 | 48 |
|  | Reduction (%) | >70 | 81 |
| 25% dilution | CONTROL | >100 | 150 |
|  | With Composition | 70 | 40 |
|  | Reduction (%) | >30 | 73 |

The data obtained for ammonia and hydrogen sulphide indicated significant reductions in levels of these gases had occurred in the presence of the composition of the invention at all dilutions. As the dilutions progressed from neat to 50% to 25% there was a stepwise reduction in percentage reductions in both cases.

Tests for Dimethyl Sulphide and Methyl Mercaptan

Similar procedure as before but this time a 5 L capped plastic container was used. 12 ml of leachate was placed in the container, 90 seconds were allowed to pass and the readings taken for both methyl mercaptan and dimethyl sulphide. 12 ml of neat composition of the invention was added to the container, 90 seconds was allowed to pass to allow the odour to develop and the gas in the container was retested.

Results

There was no evidence for the presence of methyl mercaptan in the leachate. However in the case of the dimethyl sulphide, 3 ppm was present before treatment and after treatment with the composition there was a zero reading for this compound.

Further Tests Using Draeger® Tubes with Methyl Mercaptan

A new experimental procedure was devised so that the foul-smelling additive, methyl/ethyl mercaptans in commercial propane gas was used as a controlled source of mercaptans. The presence of the inert hydrocarbon gases, methane, propane butane are believed to have no deleterious effect on the tests A 5 liter plastic container was filled with propane gas from a cylinder by downward displacement of water and the sample then tested for $CH_3/C_2H_5SH$ with appropriate Draeger® Tubes, which had a 0.5-5 ppm mercaptan range. The container was sealed with a plastic cover with an 8 mm hole drilled through the lid. The gas seal being achieved using polythene film.

The test procedure was carried out in duplicate, the control level of mercaptans was >5 ppm (possibly <10 ppm).

After vigorously shaking with near composition according to the present invention for 1 minute, the gas was again sampled for mercaptans with Draeger® Tubes. It was found that the residual level of mercaptans was between 0 and 0.5 ppm.

This experiment was repeated using a commercial residential odour treatment product called Febreze® manufactured and sold by Proctor & Gamble.

With neat Febreze® the tests showed that the level of mercaptans remained unchanged with more than 5 ppm of mercaptan present after treatment in the container after 1 minute of mixing.

The invention claimed is:

1. An aqueous composition consisting of:
   a) copper sulfate,
   b) one or more copper organic acid salts at least one of which is copper citrate,
   c) hydrogen peroxide,
   d) one or more diols having from 3 to 10 carbon atoms in the alkyl moiety, and
   e) one or more non-ionic alcohol ethoxylate surfactants, and
   f) water, wherein the aqueous composition is a stable aqueous solution.

2. A method of malodour control comprising:
   deploying an aqueous composition according to claim 1 to a source of malodour.

3. The method of malodour control of claim 2, wherein the deploying step includes delivering the aqueous composition to a malodour containing environment as an aerosol.

4. A malodour treatment kit consisting of:
   a) first composition consisting of copper sulfate and copper citrate; and
   b) a second composition being a stabilized aqueous hydrogen peroxide composition consisting of hydrogen peroxide; one or more diols having from 3 to 10 carbon atoms in the alkyl moiety; one or more non-ionic alcohol ethoxylate surfactants; and water.

5. The aqueous composition of claim 1, wherein the hydrogen peroxide is present in an amount from 1 to 20% by weight.

6. The aqueous composition of claim 1, wherein the non-ionic surfactant is an alcohol ethoxylate of the following general structure (I):

$$R-(OCH_2CH_2)_n-OH \qquad (I)$$

wherein R is a hydrocarbon group having from 8 to 22 carbon atoms and n number is the number of molecules of ethylene oxide present.

7. The aqueous composition of claim 6, wherein n is from 3 to 40.

8. The aqueous composition of claim 6, wherein the diol of d) is a vicinal diol.

9. The aqueous composition of claim 8, wherein the vicinal diol is propane-1,2-diol.

10. The aqueous composition of claim 6, wherein R is a hydrocarbon group having from 8 to 15 carbon atoms.

11. The aqueous composition of claim 6, wherein R is a hydrocarbon group having from 9 to 11 carbon atoms.

12. The aqueous composition of claim 6, wherein n is from 3 to 30.

13. The aqueous composition of claim 6, wherein n is from 3 to 20.

14. The aqueous composition of claim 6, wherein n is from 5 to 10.

15. The aqueous composition of claim 6, wherein n is from 5 to 9.

* * * * *

UNITED STATES PATENT AND TRADEMARK OFFICE
CERTIFICATE OF CORRECTION

PATENT NO. : 8,834,939 B2  Page 1 of 1
APPLICATION NO. : 13/201136
DATED : September 16, 2014
INVENTOR(S) : Peter Carty et al.

It is certified that error appears in the above-identified patent and that said Letters Patent is hereby corrected as shown below:

In the Claims

Column 16, Line 32, Claim 6:

After "atoms and n"
Delete "number".

Signed and Sealed this
Sixteenth Day of June, 2015

Michelle K. Lee
*Director of the United States Patent and Trademark Office*